(12) United States Patent
Benjauthrit et al.

(10) Patent No.: US 10,888,283 B1
(45) Date of Patent: Jan. 12, 2021

(54) COVID-19 SYMPTOMS ALERT MACHINE (CSAM) SCANNERS

(71) Applicants: Boonsieng Benjauthrit, La Canada, CA (US); Sorapod B. Benjauthrit, La Canada, CA (US); Vatcharee L. Benjauthrit, La Canada, CA (US); Kamolchanok J. Benjauthrit, La Canada, CA (US)

(72) Inventors: Boonsieng Benjauthrit, La Canada, CA (US); Sorapod B. Benjauthrit, La Canada, CA (US); Vatcharee L. Benjauthrit, La Canada, CA (US); Kamolchanok J. Benjauthrit, La Canada, CA (US)

( * ) Notice: Subject to any disclaimer, the term of this patent is extended or adjusted under 35 U.S.C. 154(b) by 0 days.

(21) Appl. No.: 16/917,896

(22) Filed: Jun. 30, 2020

(51) Int. Cl.
  *A61B 5/00* (2006.01)
  *G16H 40/67* (2018.01)
  (Continued)

(52) U.S. Cl.
  CPC ............ *A61B 5/746* (2013.01); *A61B 5/0022* (2013.01); *A61B 5/01* (2013.01); *A61B 5/055* (2013.01);
  (Continued)

(58) Field of Classification Search
  CPC ......... A61B 5/0022; A61B 5/01; A61B 5/055; A61B 5/0816; A61B 5/0823;
  (Continued)

(56) References Cited

U.S. PATENT DOCUMENTS

| 9,589,219 B1 * | 3/2017 | Gonzales, Jr. | ..... G01R 33/0206 |
| 2004/0050694 A1 * | 3/2004 | Yang | ................... G01N 27/3273 204/403.02 |

(Continued)

*Primary Examiner* — Ojiako K Nwugo
(74) *Attorney, Agent, or Firm* — Michael D. Eisenberg

(57) ABSTRACT

A COVID-19 Symptoms Alert Machine (CSAM) scanner, or apparatus, is described herein. This apparatus employs Artificial Intelligent (AI) technology in combination with the latest mobile device technology (viz. smart phone/smart watch) to quickly help track down people who have COVID-19 symptoms anywhere and anytime, isolate them, and professionally handle them, not allowing SARS-CoV-2 virus to spread. CSAM automatically measures body temperature and assesses lung conditions such as pulmonary fibrosis and B-lines (for asymptomatic people), and other current health vital information (CHVI), furnished by the participant, such as fever, sore throat, headache, and body ache to generate an alert signal when COVID-19 symptoms are found significant and to send it out to a COVID-19 control center. The alerted participant is then immediately required to go to the COVID-19 control center or be picked up by a special COVID-19 emergency vehicle for isolation and further evaluation and testing. If the testing turns out to be COVID-19 positive, the participant will be quarantined and treated appropriately according to COVID-19 protocol until he/she is tested COVID-19 negative. In the meantime, people who have been in close physical contact with this participant will be alerted and requested to be immediately checked for COVID-19 symptoms. If anyone is found to have COVID-19 symptoms, then he/she must go through the same protocol. The process is repeated until all people in the cluster are tested COVID-19 negative. This will ensure that SARS-CoV-2 virus for this cluster has been completely eliminated. A rapid deployment of this type of apparatus throughout communities where people tend to congregate (Continued)

such as superstores, supermarkets, and any other establishments, small or large, can help to contain the rapid spread of the disease, as well as to give more confidence to the general public. People, who pass through this apparatus without an alert signal, should feel more confident in carrying out their activities, though social distancing and other COVID-19 precautionary requirements should still be maintained. The concept can be further expanded to cover shopping malls, concert halls, sports arenas, and any other large events including highways and freeways with the help of mobile phone technologies, transponders, and other mobile devices. By working on the 0.6% (around 2 million infected people in the US as of June 2020) quickly and effectively, instead of on the 99.4% (330 million, the remaining population) by locking people at home and closing down all businesses and activities; we can save a significant amount of money and hassles. (A long lockdown can also lead to a collapse of our economy and can consequently lead to a worldwide calamity.) In this way the 99.4% will not be burdened with the virus problem and can live normally without having to take any test. It is probably the only effective approach in solving the COVID-19 problem at the moment because vaccines and known COVID-19 cures are not yet available. Even if SARS-CoV-2 vaccines are available presently, they may not be practical to implement economically and operationally in time to contain the virus worldwide due to the massive amount of people (viz. over 7 billion).

14 Claims, 7 Drawing Sheets

(51) Int. Cl.
*G16H 50/30* (2018.01)
*G16H 50/80* (2018.01)
*G16H 40/20* (2018.01)
*G06Q 50/26* (2012.01)
*G16H 15/00* (2018.01)
*G06Q 10/10* (2012.01)
*G16H 10/20* (2018.01)
*G16H 50/50* (2018.01)
*A61B 5/01* (2006.01)
*A61B 8/08* (2006.01)
*A61B 6/03* (2006.01)
*A61B 5/055* (2006.01)
*A61B 5/08* (2006.01)
*G16H 10/65* (2018.01)
*G07C 9/15* (2020.01)
*G16H 50/20* (2018.01)
*G06K 7/10* (2006.01)

(52) U.S. Cl.
CPC .......... *A61B 5/0816* (2013.01); *A61B 5/0823* (2013.01); *A61B 5/4011* (2013.01); *A61B 5/4017* (2013.01); *A61B 6/032* (2013.01); *A61B 8/08* (2013.01); *G06Q 10/107* (2013.01); *G06Q 50/265* (2013.01); *G16H 10/20* (2018.01); *G16H 10/65* (2018.01); *G16H 15/00* (2018.01); *G16H 40/20* (2018.01); *G16H 40/67* (2018.01); *G16H 50/30* (2018.01); *G16H 50/50* (2018.01); *G16H 50/80* (2018.01); *G06K 7/10297* (2013.01); *G06Q 2240/00* (2013.01); *G07C 9/15* (2020.01); *G16H 50/20* (2018.01)

(58) Field of Classification Search
CPC ..... A61B 5/4011; A61B 5/4017; A61B 6/032; A61B 8/08; G16H 40/67; G16H 40/20; G16H 40/50; G16H 50/50; G16H 15/00; G16H 50/30; G16H 50/80; G16H 10/20; G16H 10/65; G06Q 10/107; G06Q 50/265
USPC ........................................................ 340/5.52
See application file for complete search history.

(56) References Cited

U.S. PATENT DOCUMENTS

| | | | |
|---|---|---|---|
| 2011/0307039 A1* | 12/2011 | Cornell | A61F 7/0085 607/105 |
| 2014/0247153 A1* | 9/2014 | Proud | G08B 23/00 340/870.09 |
| 2019/0108318 A1* | 4/2019 | Bagan | G16H 40/67 |

* cited by examiner

CARD HOLDER INFORMATION — 26

Name: First Middle Last
Current Address:
Home Phone:      Mobile Phone:

QR

20

CURRENT HEALTH VITAL INFORMATION
Have you been infected by SARS-CoV-2?
  o  Yes     o No
If yes, when? __MM/DD/YY_____
Mark all applicable symptoms:
o Fever                    o Muscle pain
o Cough                    o Headache
o Shortness of breath or   o Sore throat
  difficulty breathing     o Loss of taste or smell
o Chills                   o COVID-19 toes
o Repeated shaking with chills  o Pink eyes
o B-line or other lung ultrasound indicator

CSAM Action
1. Triggers an alert either visual, sound, or both.
2. Send an alert data to
   A. Participant's cell phone and email address
   B. GCSHC 's phone and email address
3. Print out an alert data at the CSAM scanner.

Host Action
1. Assist the alerted participant as much as possible.
2. Clean and disinfect anything that was touched by the alerted participant.
3. Inform other participants of the incidence and encourage them to go through the CSAM scanner if they have not done so.

Participant Action
1. Wash hands and wear an N95 mask.
2. Exercise social distancing.
3. Get printed materials from CSAM scanner.
4. Try not to touch anything as much as possible.
5. If came with someone, inform them of the fact and tell them to go through the CSAM scanner as soon as applicable.
6. Clean and disinfect vehicle.
7. If came alone, participant can drive to a GCSHC alone.
8. Participant can always request

Government COVID-19 Symptoms Handling Center (GCSHC)
1. Double check all alerted COVID-19 related symptoms.
2. Administer an appropriate COVID-19 test.
3. Appoint a case coordinator who will handle the case:
   a. Explains the advantages and disadvantages of home quarantine and outside quarantine.
   b. For those who can afford to stay home, the government will supplement any additional needs and expenses.
   c. For those decide to go to a government furnished facility, all expenses will be included.
   d. For both cases, a healthcare worker will be assigned to look after their health conditions.
   e. Gather information (both contact and health) of close contacts of the alerted participant.
   f. Inform those close contacts and order them to go through CSAM scanner as soon as possible.
   g. Ask all those close contacts to see if they know or aware of anyone of their close contacts has COVID-19 symptoms. If they do, tell them to report to GCSHC as soon as possible if they are not already under any care of any GCSHC.
   h. If the COVID-19 test result is negative, the participant can continue their existing self-quarantine as desired until the time of 14 days is achieved. After that, the participant can return to the normal life.
   i. If the COVID-19 test result is positive, the alerted participant will become a COVID-19 patient and will be under the jurisdiction of COVID-19 patient guideline.

FIG. 6B

Normal posterior lung

COVID-19 case posterior lung

COVID-19 SYMPTOMS ALERT MACHINE (CSAM) SCANNERS

BACKGROUND OF THE INVENTION

This instant invention relates generally to a class of apparatuses that employ Artificial Technology (AI) (i.e., knowledge base) to solve complex problems and more specifically it relates to a COVID-19 symptoms detection and identification. However, the process employed herein is somewhat simple but can be eventually evolved into a more intelligent process.

COVID-19 is a respiratory sickness caused by Severe Acute Respiratory Syndrome (SARS) novel coronavirus (CoV-2) [SARS-CoV-2], which is a mutated strain of SARS coronavirus (i.e. SARS-CoV-1), a close relative of the Influenza strain. It is believed to have originated in Wuhan, China, since September 2019 and currently spread worldwide to become a pandemic disease. SARS-CoV-2 is highly contagious and deadly, and can spread rapidly through nose and mouth. Once gets to the lung, it can cause significant lung damages, if the subject is physically weak, to the point where the subject cannot breath and as a result die. So far (May 5, 2020), there are over 3.5 million people worldwide have been inflicted and over 251,000 have died from COVID-19 [according to the statistics from the John Hopkins University]. Currently, there are no known drugs that can be used to kill the virus, only a few medications such as Remdesivir, Hydroxychloroquine, HIV drugs lopinavir and ritonavir, provided by AbbVie as Kaletra and flu medication oseltamivir, sold by Roche Holding and Chugai Pharmaceutical as Tamilflu that can be used to shorten the recovery time or to vastly improve the patient's condition. Other potential drugs have been identified by Professor Kamlendra Singh of the University of Missouri are 5-fluorouracil, ribavirin, and favipiravir. Vaccines for this virus are also not yet available. It will take at least a year or even many years, before a viable vaccine will be available. Even there is an effective vaccine available, with the world population of over 7 billion people, it will not be practical monetarily and operationally to implement a worldwide vaccination process in a timely manner. So the only way to combat with this virus is to try to identify those already infected, as well as those closely associated with the victims, with this virus and isolate them from the mass so their infection will not spread further.

To slow down the spread of the virus, the most used approach by various countries around the world is to order their citizens to stay home or what is typically referred to as a lockdown. Thus, all businesses and activities around the globe have been halted. However, people have to eat and maintain their livelihoods, after a few weeks, these lockdowns need to be lifted; otherwise, people will soon starve to death and chaos will inevitably follow. As the world number one economic leader (486 million in Gross Domestic Product (GDP), if the U.S. financially collapses, the rest of the world will certainly suffer greatly.

It should be noted that the current general practice in preventing the spread of COVID-19 is to maintain social distancing of six feet or more, wash hands often, and wear a mask in public. Japanese doctors who treat COVID-19 recommend to keep mouth and throat moist constantly by taking a few sips of water or other liquids every 15 minutes. This way viruses will be washed down the oesophagus into the stomach where they will be killed by stomach acid. Otherwise, they will enter into the windpipes and eventually in to the lung. A Chinese doctor indicates that the virus can stay in the throat for 4 days and will cause sore throat after that. Drinking water or goggle the throat with salt water or vinegar can help to get rid of them. Dr. Tang Luhong of Jiangnan University, Wuxi, in China, who has been working on herbal research using garlic in place of antibiotic medicine since 2014 has discovered that the compound Allicin found in garlic can inhibit, kill, and prevent SARS-CoV-2. The reason for this is Allicin can inhibit the production of emzyme protease, which is required by SARS-CoV-2 in their growth. Actually, Allicin is also effective on SARS-CoV-1 as well as MERS. Dr. Tang has used the garlic vapor to treat both vulnerable and infected patients since February 2020 and have found it to be effective. His treatment is to crush fresh garlic and inhale its smell into the lung through the mouth and hold it as long as possible.

With all technologies and capabilities that human beings have accumulated over the past centuries, there is no reason we cannot handle such calamity in a reasonable way, without causing a worldwide disaster. We are able to send human beings to the moon and spacecraft to Mars and other planets. To handle SARS-CoV-2 by the method of lockdown, i.e., blindly ordering people to stay home and all businesses to shut down is a little bit absurd. We plan to and actually have spent trillions of dollars to shore up the livelihood of the citizens and the economy. Yes, we are in a dire need of SARS-tCoV-2 vaccines and drugs that can slaughter them. But in the meantime, with all the technologies, capabilities, and skills that we have accumulated over centuries, we should do a lot better than what have already been done. By employing a little statistical skills, basic technologies and tools, and human ingenuity; we should be able to tackle this little bug reasonably. Let us see. We currently have around 332 million people in the U.S. From COVID-19 prospective, they consist of normal people, vulnerable (heart disease (18.2 m), hypertension (77.9 m), diabetes (34.2 m), respiratory disease (65 m) (around 200 m)), COVID-19 survivors (183 k), and SARS-CoV-2 infected (1.32 m or around 2 m). Instead of working on the whole population (332 m) at the same time (i.e., lockdown), if we put emphasis on those infected (2 m), and give a warning to those vulnerable (200 m); we can save some significant money and lives and still maintain a fairly healthy economy. Mathematically, we really want to work on the 0.6% (100*2 m/332 m), rather than the 99.4%. For example, if we spend $1000 on each person in handling the situation, it would cost $3.32 trillion for the whole population of 332 million, but only 2 billion if we work mainly on the infected people. Instead, if we spend only $10 for each of the healthy people ($1.32 billion), $50 on each vulnerable ($10 billion), and $1000 on the infected ones ($2 billion); it will end up costing a total of $13.32 billion, which is very manageable.

Regardless of what we have to do, we still need to have a mean to identify SARS-CoV-2 infected people at large. The common approach is to use handheld infrared scanner to measure the temperature of the forehead. In China, they even have smart helmets for police to check body temperature of surrounding people and these smart helmets are also being distributed to other countries like the Emirate. These remote temperature detections are useful but there are not very convenient and widely employed. There still needs for better equipment in fighting to contain SARS-CoV-2.

SUMMARY OF THE INVENTION

A primary objective of this invention is to provide an apparatus to overcome the short comings of the prior art devices.

Another objective of this apparatus is to provide an apparatus that can detect the body temperature of the participant who will walk through the apparatus using infrared signals or other means and other health vital data relating to COVID-19. The health vital data is to be provided through a paper card, magnetic stripe card, smart (both contact and contact less) card, and an electronic means such as a computer, an iPad, or a smart phone and other wide distance technology such as RFID technology. The health vital data will include at least the following information, to be furnished by the participant:

Have you been infected by SARS-CoV-2? If yes, when?
Do you have any of the following symptoms?

| | |
|---|---|
| Fever | Cough |
| Shortness of breath or difficulty breathing | Muscle pain |
| | Headache |
| Chills | Sore throat |
| Repeated shaking with chills | New loss of taste or smell |
| B-line or other lung ultrasound indicator | COVID toes |
| | Pink eye |

This list of items may be updated or improved by the recommendation from the healthcare agencies.

There are many ways one can generate the items above. One is to gauge oneself, while another may have to consult with family members, family physician, and check with publicly available facilities such as lung ultrasound scanner post (LUSP). For example, to check for shortness of breath or difficulty breathing, one may simply follow the recommendation of the Stanford hospital board on coronavirus as follows: Since SARS-CoV-2 may not show sign of infection for many days and by the time they have fever and/or cough and go to the hospital, the lung is usually 50% Fibrosis and then it would be too late. Taiwan experts recommend taking a deep breath and hold for more than 10 seconds. If one can complete it successfully without coughing, without discomfort, stiffness, etc., then it indicates that there is no Fibrosis in the lung, so the bullet on shortness of breath or difficulty breathing can be skipped.

An additional objective is to provide an apparatus that can generate an alert signal when the conditions of COVID-19 have been found in the data collected from the participant, send the alert signal to a relevant healthcare center linked to the apparatus so further actions can be proceeded, and can print the alert information so the participant can take to a health center for further processing.

A further objective is to provide an apparatus that is convenient and simple to use but useful.

A still further objective is to provide an apparatus that is economical in cost to manufacture and to be localized.

Other objectives may be found as the detailed description is elaborated below.

Though the above objectives described above can be illustrated through the following drawings and discussions, the embodiment of the invention is not limited to them and is covered in the appended claims.

BRIEF DESCRIPTION OF THE FIGURES AND IDENTIFICATION NUMBERS

The drawings in the figures can be briefly described as follows:

FIG. 5 is a diagram of typical contents of the Current Health Vital Information (CHVI) magnetic card.

FIG. 6B is a detailed protocol that each entity outlined in FIG. 6A should execute.

| Identification numbers are: | | |
|---|---|---|
| 1 - A main scanner structure | 12 - Printer | 22 - Blank CHVI card holder box |
| 2 - CHVI data entry area | 13 - A CHVI card data entry stand | 23 - Card slot |
| 3 - Participant | 14 - Monitor screen | 24 - A mouse |
| 4 - Data entry stand | 15 - Keyboard | 25 - QR code on CHVI card front |
| 5 - Information desk personnel | 16 - CHVI Card writer | 26 - QR code located inside CHVI card (same as 25) |
| 6 - Information center | 17 - Magnetic card | |
| 7 - Information desk | 18 - CHVI card label | 27 - CHVI card reader |
| 8 - Main CSAM scanner | 19 - CHVI card owner name | 28 - Door |
| 9 - Human body temperature scanner | 20 - Card holder information section | 29 - Turnstile |
| 10 - Central Processing Unit (CPU) | 21 - Current health vital information | 30 - Turnstile side stand |
| 11 - Alert indicator light | | 31 - Turnstile door hinge |

DETAILED DESCRIPTION OF PREFERRED EMBODIMENTS

Figure 1:
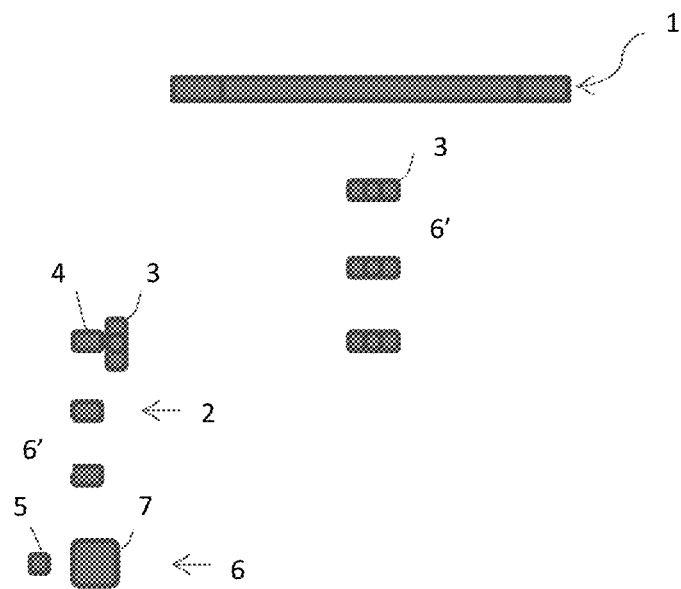
FIG. 1 is a schematic diagram of a COVID-19 symptoms alert machine (CSAM) system, consisting of the main scanner, data entry stands, and an information station.
Figure 3:
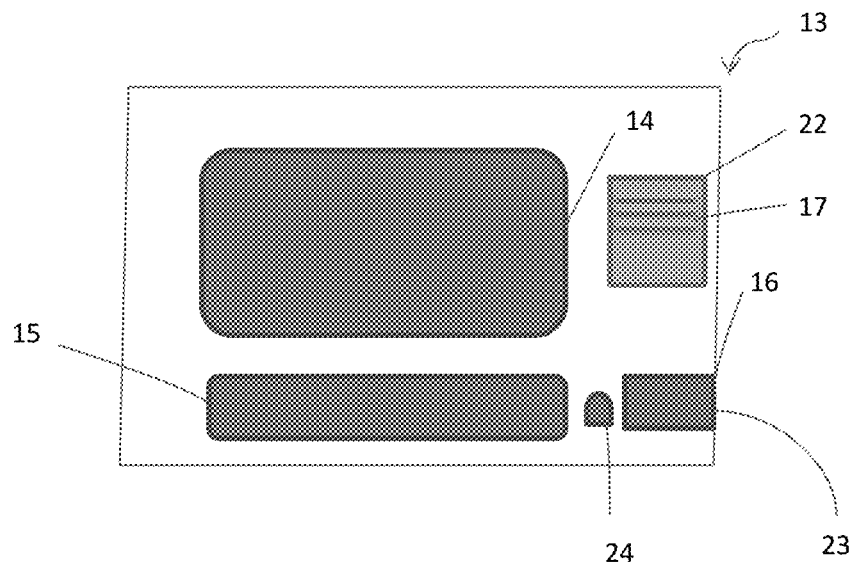
FIG. 3 is a schematic diagram of typical components of a data entry stand.
Figure 4:
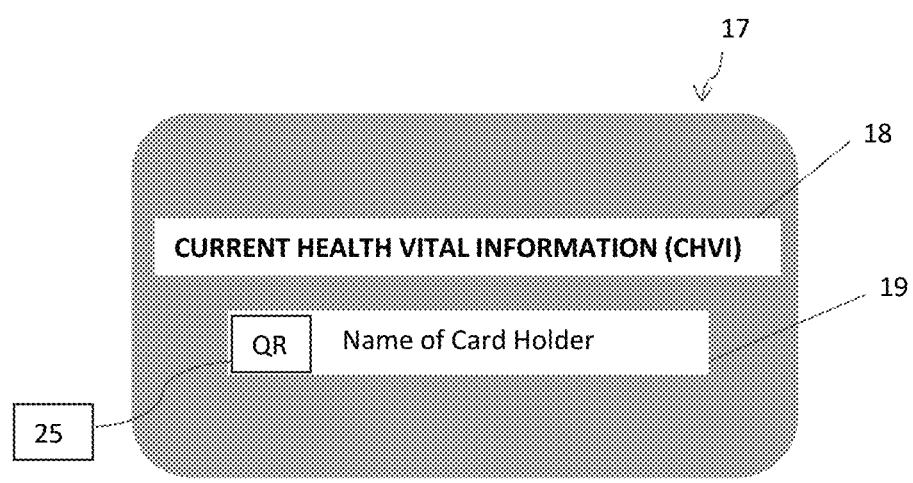
FIG. 4 is a schematic diagram of a typical Current Health Vital Information (CHVI) magnetic card.

Though all features of this invention cannot be detailed herein, the preferred embodiments are now illustrated and described in the following figures. FIG. 1 identifies all essential elements of a COVID-19 symptoms alert machine, consisting of a main scanner structure 1, data entry stands 4, and an information center 6 with information center personnel 5. A participant; a worker, a customer, a sport fan, or a concert audience; 3 would initially freely register to obtain a Current Health Vital Information (CHVI) card 17 at a data entry stand 4, located in the CHVI data entry area 2. The CHVI card 17 can be a magnetic card 17, a contact microchip card, a non-contact microchip card, or a Radio Frequency Id (RFID) card. Each data entry stand 4 (FIG. 3) has a monitor screen 14 to display items 20 and 21 (FIG. 5) that the participant 3 must enter in order to generate a current health vital information into a magnetic card 17, a standard computer keyboard 15 and a mouse 24 for used to enter the data, and a magnetic card writer 16. For a new participant, a new magnetic card 17 can be fetched from a blank magnetic card holder box 22. For those participants who already have a CHVI card and want to update their cards, they can simply insert their cards into the card writer 16 at slot 23. Each new participant needs to first enter their card hold personal information in the Card holder information box 20 through the keyboard 15 and mouse 24. After that, the participant can address questions in the Current Health Vital Information 21 through the keyboard 15 again. If already registered, the participant only needs to update the current health vital information 21, unless he or she needs also to update such information. Once done, the participant can complete by hitting enter at the keyboard 15 or click mouse 24. The CHVI card writer 16 will write all entered data on the magnetic card 17, as well as to generate a QR code and records it on the card. It will also print the name of the participant and the corresponding QR code 25 on the front of the card. After finishing the card, the participant can also use his or her mobile phone to record the QR code 26 for the main scanner to scan it in place of the magnetic card 17 if applicable.

In order to reduce surface contacts, one other possible implementation of a data entry stand is to combine a monitor screen 14, keyboard 15, and a mouse 24 into one unit of screen with a soft keyboard and a soft mouse. Actually, the whole data entry stand 4 can be replaced with an application that smart phone, smart watch or any other smart mobile device can be uploaded so the CHVI data can be entered privately.

For asymptomatic participants, who usually do not feel their COVID-19 symptoms but feel suspiciously that they may have it should go to a LUSP, which will be government furnished place to be located at a widely known business or public facilities such as a super market, a Starbucks, a seven eleven, a public library, etc. Each LUSP will be manned by trained clinicians, which can be volunteers. These trained clinicians should know how to properly handle lung ultrasound transducers or probes so their results are reliable. Actually, these LUSPs are available for free to anyone who feels that he/she may have COVID-19 symptoms anytime, even daily if it is warranted. After the examination, each LUSP will print out the result of the scan so the participant can keep for a record or reference.

Figure 9:
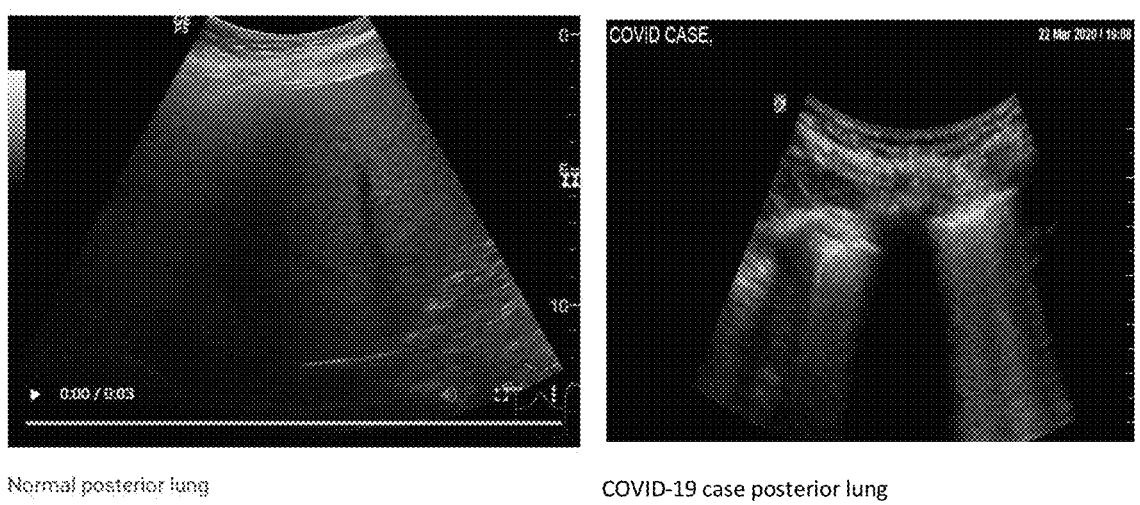
FIG. 9 is a comparison of B-line of a normal posterior lung ultrasound and a COVID-19 case.

A sample of a normal B-line of posterior lung and a COVID-19 case is shown in FIG. 9.

In order to make the fight of COVID-19 effective, we may have to introduce an international law to punish people who enter untruthful CHVI and/or refuse to have lung ultrasound scan when they have potential COVID-19 symptoms.

Figure 2:
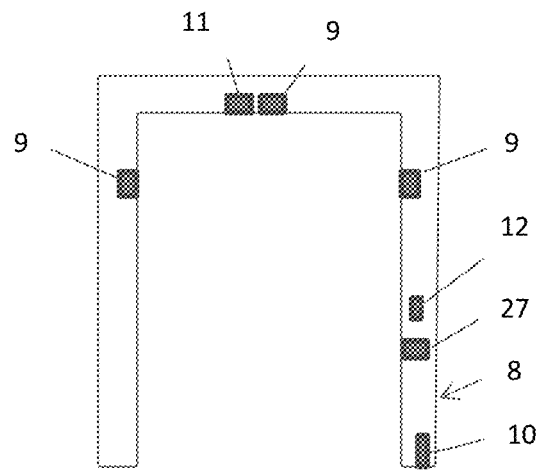
FIG. 2 is a schematic diagram of a side view of the main scanner, showing various subsystems.

A schematic drawing of the main scanner body is shown in FIG. 2, depicting the frame 8 attached with 3 human body temperature scanners, or infrared sensors 9. In the real version of this main body of this scanner may contain more or less than 3 sensors and at some other convenient and effective positions. Above or any other appropriate location, is the place for an alert signal assembly 11. Similarly, a QR scanner assembly 17 can be located next to the human body temperature scanners, or infrared sensor 9 or any other move convenient and effective location n. When a participant walks through the scanner assembly, the human body temperature scanners, or infrared sensors 9 will sense the body temperatures and an average value (or any other formula deemed most accurate value) of these temperatures will be calculated. This calculation can be achieved via hardware or software, depending on the implementer. The final scanned body temperature and the data obtained from the magnetic card 17/QR picture are then sent to the main Central Processing Unit (CPU) or a computer 10. Besides control and calculation, CPU 10 is also contains all smart phone features such as WIFI communication, high volume data storage, etc. The CPU or computer will determine to see if a COVID-19 Symptoms Alert assembly should be activated. One such algorithm is given below:

A COVID-19 Symptoms Alert Signal is activated when
1. Body temperature is >=99.5° F. (37.5° C.).
2. Condition of Item 1 and one or more of conditions of CHVI.
3. Yes on CHVI.
4. Condition of Item 3 and one or more of conditions of CHVI.
5. Two or more of conditions of CHVI.

Once CSAM alert is activated, the scanner will print all the information of the participant, the conditions that trigger the alert, and the names, addresses, and phone numbers as well as email addresses of COVID-19 processing centers available. Instructions on what to do and how to go to those appropriate centers. A detailed procedures of what to do and how to proceed after an alert signal is activated is beyond the scope of this patent and will not be described herein. However, in order to prevent or eliminate the spread of SARS-CoV-2 virus, a rigorous procedure should be in place to handle such a situation. A requirement for the participant to right away to clean his or her hands, wear an N95 mask, all equipment touched by the participant should be thoroughly cleaned and disinfected. The participant should be isolated. If he came with someone, those came with him or her should also be checked and recorded, and be closely followed up until all parties are all cleared. For example, if A is found to generate an alert signal, then A must be sent to test for COVID-19 right away. A will be isolated after the test until the test result is known. In the meantime, anything that has been touched by A should be cleaned and disinfected. Any person who has been associated with A will also be identified and followed up.

Those participants who pass the main CSAM scanner 8 with no alert activation are ready to proceed into the establishment with confidence, but the general protection practices such as wearing a mask, washing hands, maintaining social distancing, etc. should still be observed when one can.

Figure 6A:
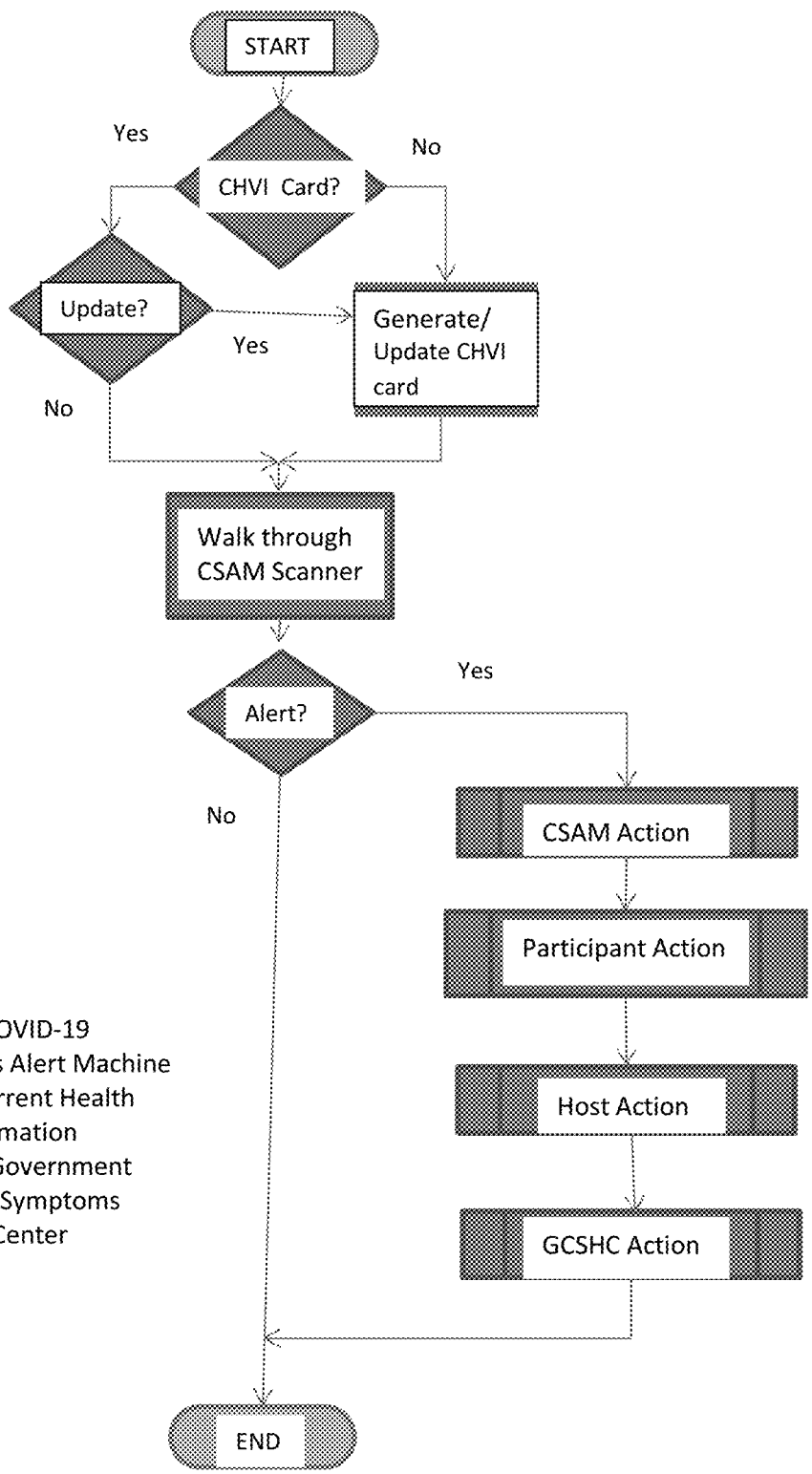
FIG. 6A is an operational algorithm of how CSAM works.

In operation, the CSAM scanner is operated as follows. Participants arrive at their target place, whether it is an office building, a whole sale store like a Home Depot, a theater, or a sport complex. If they are new to the place, they may inquire about the how to go about getting into the place at the information desk 6. For those new to the CSAM scanner, they will have to generate a COVID-19 Health Symptoms Vital Information (CHVI) card 17 at a CHVI card writer stand 3 located at a CVHI data entry area 2, where these stands are set at least 6 feet apart. They type in their names, address, phone numbers and email address in the Card Owner Information section and answer all COVID-19 symptoms questions with the keyboard and mouse provided. Once they finish making a CHVI card, they can walk through the CSAM scanner. They have to swipe their CHVI card at the card reader located at the main CSAM scanner 8. If they have to line up behind the scanner, they have to observe 6-foot apart protocol. If there is no alert signal, they can proceed to enter the establishment. If an alert signal is triggered, then they will have to follow the instruction given in a print out at printer 12. The whole operation is captured in the algorithm provided in FIG. 6A and FIG. 6B.

Figure 7A:
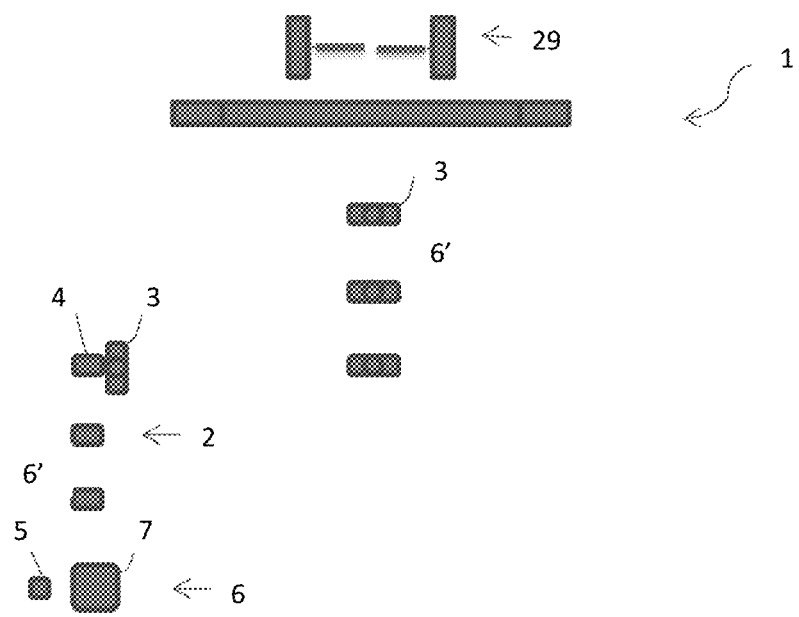
FIG. 7A is another possible version of the preferred embodiment where a turnstile is added to it.
Figure 7B:
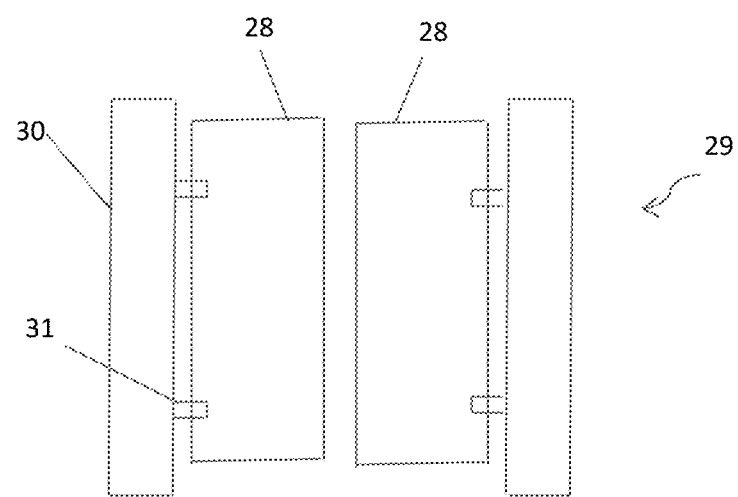
FIG. 7B is a side view of a possible turnstile.

In another embodiment, the CSAM scanner includes a turnstile 29 behind the main CSAM scanner 8 in order to have a better control of participants, as shown in FIG. 7A and FIG. 7B. In the event a COVID-19 symptoms alert indicator light sounds off, the participant may not be allowed to proceed into the establishment. In this case, the CPU would send a command to lockdown the turnstile doors 28.

These doors are held to the turnstile side stands 30 with hinges 31, which are under control by the CPU.

Figure 8:
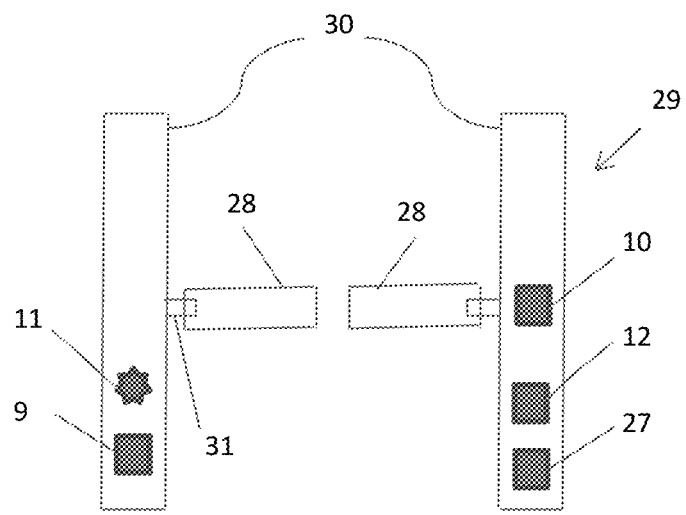
FIG. 8 is a turnstile with all CSAM elements embedded that can be used in place of a main CSAM scanner.

Actually, in some other embodiment, the main CSAM scanner 8 can be only a turnstile 29 with all the elements located on the frame to be located on the two side stands 30 of the turnstile 29 as shown in FIG. 8. In such embodiment, the gantry will not be needed. This type of embodiment may have a disadvantage that another type of supplemental device such as a Computed Tomography (CT) scanner or a Magnetic Resonance Imaging (MRI) may not be conveniently installed unless the side stands are modified to accommodate such implementation. CT scanner or MRI scanner has a potential to be used to diagnose the condition of the lung. Other technologies such as ultrasound may also have a potential to help in identifying symptoms of COVID-19.

In still another embodiment, the main CSAM scanner 8 can be a giant gantry on an entrance of a big establishment such as Disneyland, a shopping mall, or a sport arena. In this case, the communication and data collection will be through a mobile phone, smart watch, or any other electronic gadget of similar nature.

In still another embodiment, the main CSAM scanner 8 can be giant gantries on freeways. Again the communication and data collect will be similar to the one discussed above.

What is claimed is:

1. A COVID-10 Symptoms Alert Machine (CSAM) scanner comprising:
   a main CSAM scanner, including:
   a human body temperature scanner for scanning a body temperature of a participant;
   a current health vital information (CHVI) card, provided by the participant, containing information of the participant and COVID-19, and configured for being read by the CSAM scanner; and
   a Central Processing Unit (CPU) and a memory having computer readable instructions stored thereon, that when executed by the CPU, cause the CPU to controlling the operation of the CSAM scanner.

2. The CSAM scanner of claim 1, wherein the CPU is configured to trigger a COVID-19 symptoms alert, to print out COVID-19 symptoms information, to send the COVID-19 symptoms information to a phone number and an email address of the participant and to a government COVID-19 symptoms handling center via a smart mobile phone-like device and an email address, the COVID-19 symptoms information including:
   a. A COVID-19 information center to handle COVID-19 related activities; and
   b. a set of CHVI card data entry stands, where the participant can enter and modify their current health vital information on the CHVI card.

3. The CSAM scanner of claim 1, wherein the CHVI card is a magnetic card, a contact microchip card, a non-contact microchip card, or a Radio Frequency Id (RFID) card.

4. The CSAM scanner of claim 1, further comprising:
   an exit of the main CSAM scanner;
   an electronic turnstile gate installed at the exit of the main CSAM scanner, for opening when an alert is present and closing when no alert is present, according to a command from the CPU.

5. The CSAM scanner of claim 1, further comprising:
   at least one device for assessing organ damage and providing supplemental information about the COVID-19 symptoms to the CSAM scanner, wherein the least one device is a lung ultrasound (LUS) scanner, a Computer Tomography (CT) machine, or a Magnetic Resonance Imaging (MRI) machine.

6. The CSAM scanner of claim 4, further comprising:
   at least one device for assessing organ damage and providing supplemental information about the COVID-19 symptoms to the CSAM scanner, wherein the least one device is a lung ultrasound (LUS) scanner, a Computer Tomography (CT) machine, or a Magnetic Resonance Imaging (MRI) machine.

7. The CSAM scanner of claim 5, further comprising:
   an exit of the main CSAM scanner;
   an electronic turnstile gate installed at the exit of the main CSAM scanner, for opening when an alert is present and closing when no alert is present, according to a command from the CPU.

8. The CSAM scanner of claim 5, further comprising a transponder for allowing communication between the participant and the CSAM scanner; wherein:
   the CSAM scanner is configured to be installed on a structure.

9. The CSAM scanner of claim 8, wherein the structure is a gantry.

10. The CSAM scanner of claim 8, wherein the structure is a building structure over a shopping mall.

11. The CSAM scanner of claim 8, wherein the structure is a freeway.

12. The CSAM scanner of claim 5, wherein when the device is a LUS scanner, the device is configured to obtain information on lung condition from the CHVI card from an asymptomatic participant.

13. The CSAM scanner of claim 8, wherein when the device is a LUS scanner, the device is configured to obtain information on lung condition from the CHVI card from an asymptomatic participant.

14. The CSAM scanner of claim 1, wherein the symptoms comprise fever, cough, shortness of breath, sore throat, loss of taste, and loss of smell.

* * * * *